United States Patent
Forsyth et al.

(10) Patent No.: US 11,364,070 B2
(45) Date of Patent: Jun. 21, 2022

(54) ENHANCED NEEDLE ARRAY AND THERAPIES FOR TUMOR ABLATION

(71) Applicant: BOSTON SCIENTIFIC SCIMED, INC., Maple Grove, MN (US)

(72) Inventors: Bruce R. Forsyth, Hanover, MN (US); Matthew Ryan Dewitt, Charlottesville, VA (US); Hong Cao, Maple Grove, MN (US); Timothy A. Ostroot, Cokato, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 639 days.

(21) Appl. No.: 16/254,879

(22) Filed: Jan. 23, 2019

(65) Prior Publication Data

US 2019/0223943 A1    Jul. 25, 2019

Related U.S. Application Data

(60) Provisional application No. 62/620,873, filed on Jan. 23, 2018.

(51) Int. Cl.
*A61B 18/14*    (2006.01)
*A61N 1/32*    (2006.01)
(Continued)

(52) U.S. Cl.
CPC ...... *A61B 18/1482* (2013.01); *A61B 18/1477* (2013.01); *A61M 5/158* (2013.01);
(Continued)

(58) Field of Classification Search
CPC ............ A61B 18/1482; A61B 18/1477; A61B 2018/00178; A61B 2018/00107;
(Continued)

(56) References Cited

U.S. PATENT DOCUMENTS

| 5,019,034 A | 5/1991 | Weaver et al. |
| 5,370,675 A | 12/1994 | Edwards et al. |

(Continued)

FOREIGN PATENT DOCUMENTS

| JP | H1024049 A | 1/1998 |
| JP | 2013536728 A | 9/2013 |

OTHER PUBLICATIONS

StarBurst XL RFA Electrodes, Angiodynamics Inc. 2013. 2 pages.
(Continued)

*Primary Examiner* — Linda C Dvorak
*Assistant Examiner* — Christine A Dedoulis
(74) *Attorney, Agent, or Firm* — Seager, Tufte & Wickhem LLP

(57) ABSTRACT

Novel and versatile apparatuses for delivering one or more of thermal ablation and irreversible electroporation therapies to target tissue. In some examples, a device includes at its distal end a plurality of electrodes that can be advanced or retracted to pierce patient tissue, with a variable position and size shaft electrode provided near the distal end of the device to allow manipulation of therapy fields to achieve various tissue destruction field shapes. A number of method of use examples are described as well.

10 Claims, 21 Drawing Sheets

(51) Int. Cl.
*A61M 5/158* (2006.01)
*A61B 18/00* (2006.01)
(52) U.S. Cl.
CPC .... *A61N 1/327* (2013.01); *A61B 2018/00029* (2013.01); *A61B 2018/00107* (2013.01); *A61B 2018/00178* (2013.01); *A61B 2018/00547* (2013.01); *A61B 2018/00577* (2013.01); *A61B 2018/00613* (2013.01); *A61B 2018/143* (2013.01); *A61B 2018/1475* (2013.01)
(58) Field of Classification Search
CPC .......... A61B 2018/00029; A61B 2018/00613; A61B 2018/00547; A61B 2018/143; A61B 2018/1475; A61B 2018/00577; A61N 1/327; A61M 5/158
USPC ........................................................ 606/41
See application file for complete search history.

(56) References Cited

U.S. PATENT DOCUMENTS

| | | |
|---|---|---|
| 5,718,246 A | 2/1998 | Vona |
| 5,855,576 A | 1/1999 | Leveen et al. |
| 5,863,290 A * | 1/1999 | Gough ............... A61B 18/1815 606/41 |
| 6,010,613 A | 1/2000 | Walters et al. |
| 6,041,252 A | 3/2000 | Walker et al. |
| 6,043,066 A | 3/2000 | Mangano et al. |
| 6,278,895 B1 | 8/2001 | Bernard |
| 6,326,177 B1 | 12/2001 | Schoenbach et al. |
| 6,387,671 B1 | 5/2002 | Rubinsky et al. |
| 6,428,534 B1 | 8/2002 | Joye et al. |
| 6,638,277 B2 | 10/2003 | Schaefer et al. |
| 6,912,471 B2 | 6/2005 | Heigl et al. |
| 6,994,706 B2 | 2/2006 | Chornenky et al. |
| 7,245,963 B2 | 7/2007 | Draghia-Akli et al. |
| 7,306,595 B2 | 12/2007 | Ostrovsky et al. |
| 7,306,940 B2 | 12/2007 | Miklavcic et al. |
| 7,416,549 B2 | 8/2008 | Young et al. |
| 7,456,012 B2 | 11/2008 | Ryttsen et al. |
| 7,794,458 B2 * | 9/2010 | McIntyre ........... A61B 18/1477 606/41 |
| 7,799,022 B2 | 9/2010 | Fernald et al. |
| 7,850,681 B2 | 12/2010 | LaFontaine |
| 8,014,854 B2 | 9/2011 | Schroeppel et al. |
| 8,048,067 B2 | 11/2011 | Davalos et al. |
| 8,114,070 B2 | 2/2012 | Rubinsky et al. |
| 8,152,801 B2 | 4/2012 | Goldberg et al. |
| 8,211,104 B2 | 7/2012 | McCullagh et al. |
| 8,251,986 B2 | 8/2012 | Chornenky et al. |
| 8,282,631 B2 | 10/2012 | Davalos et al. |
| 8,465,484 B2 | 6/2013 | Davalos et al. |
| 8,540,710 B2 | 9/2013 | Johnson et al. |
| 8,603,087 B2 | 12/2013 | Rubinsky et al. |
| 8,647,338 B2 | 2/2014 | Chornenky et al. |
| 8,801,709 B2 | 8/2014 | Prakash et al. |
| 8,915,911 B2 * | 12/2014 | Azure ............... A61B 18/1477 606/41 |
| 8,920,416 B2 | 12/2014 | Pham et al. |
| 8,926,606 B2 | 1/2015 | Davalos et al. |
| 9,005,189 B2 | 4/2015 | Davalos et al. |
| 2001/0044596 A1 | 11/2001 | Jaafar |
| 2002/0058933 A1 * | 5/2002 | Christopherson ...... A61B 18/14 606/34 |
| 2002/0077627 A1 * | 6/2002 | Johnson ............. A61B 18/1477 606/41 |
| 2002/0107515 A1 | 8/2002 | Edwards et al. |
| 2002/0115991 A1 | 8/2002 | Edwards |
| 2003/0009110 A1 | 1/2003 | Tu et al. |
| 2004/0186468 A1 | 9/2004 | Edwards |
| 2005/0267467 A1 | 12/2005 | Paul et al. |
| 2006/0142801 A1 | 6/2006 | Demarais et al. |
| 2006/0293730 A1 | 12/2006 | Rubinsky et al. |
| 2007/0025919 A1 | 2/2007 | Deem et al. |
| 2008/0009927 A1 * | 1/2008 | Vilims ................ A61M 25/007 607/115 |
| 2008/0275445 A1 | 11/2008 | Kelly et al. |
| 2009/0247933 A1 | 10/2009 | Maor et al. |
| 2010/0023004 A1 | 1/2010 | Francischelli et al. |
| 2010/0261994 A1 | 10/2010 | Davalos et al. |
| 2011/0238057 A1 * | 9/2011 | Moss ................. A61B 18/1477 606/33 |
| 2012/0053403 A1 * | 3/2012 | Ducharme ............. A61B 1/012 600/104 |
| 2012/0059309 A1 * | 3/2012 | di Palma ............ A61M 25/007 604/22 |
| 2012/0310230 A1 | 12/2012 | Willis |
| 2012/0330299 A1 | 12/2012 | Webster et al. |
| 2013/0184702 A1 | 7/2013 | Neal, II et al. |
| 2014/0121663 A1 | 5/2014 | Pearson et al. |
| 2014/0128859 A1 | 5/2014 | Lee |
| 2014/0128936 A1 | 5/2014 | Laufer et al. |
| 2016/0113707 A1 * | 4/2016 | Sahakian ........... A61B 18/1477 606/41 |
| 2016/0113709 A1 | 4/2016 | Maor |
| 2016/0199661 A1 | 7/2016 | Willard et al. |

OTHER PUBLICATIONS

StarBurst Talon Infusion RFA Electrodes, Angiodynamics Inc. 2013. 2 pages.

Deodhar et al; "Irreversible Electroporation Near the Heart: Ventricular Arrhythmias Can Be Prevented With ECG Synchronization." AJR 196:W330-W335, Mar. 2011. Accessed on Jul. 16, 2019.

Beebe et al; "Nanosecond Pulsed Electric Field (nsPEF) Effects on Cells and Tissues: Apoptosis Induction and Tumor Growth Inhibition", IEEE Transactions on Plasma Science , 6 pages, Mar. 2002.

Kennedy et al; "Cationic Peptide Exposure Enhances Pulsed-Electric-Field-Mediated Membrane Disruption", PLOS ONE, vol. 9, Issue 3, 17 pp. Mar. 2014.

Miklavcic et al; "The Importance of Electric Field Distribution for Effective in Vivo Electroporation of Tissues", Biophysical Journal, vol. 74, pp. 2152-2158, May 1998.

Distelmaier et al; "Midterm Safety and Efficacy of Irreversible Electroporation of Malignant Tumors Located Close to Major Portal or Hepatic Veins", Radiology, vol. 285, No. 3, 1023-1031, Dec. 2017.

Rubinsky et al; "Irreversible Electroporation: A New Ablation Modality—Clinical Implications." Technology in Cancer Research and Treatment, vol. 6, No. 1, pp. 37-48, Feb. 2007.

Swartz et al; "Sparking New Frontiers: Using in Vivo Electroporation for Genetic Manipulations", Developmental Biology, 233, pp. 13-21, 2001.

Tsong, "Electroporation of Cell Membranes," Biophysical Journal, vol. 60, pp. 297-306, Aug. 2, 1991.

International Search Report and Written Opinion dated Apr. 17, 2019 for International Application No. PCT/US2019/014680.

* cited by examiner

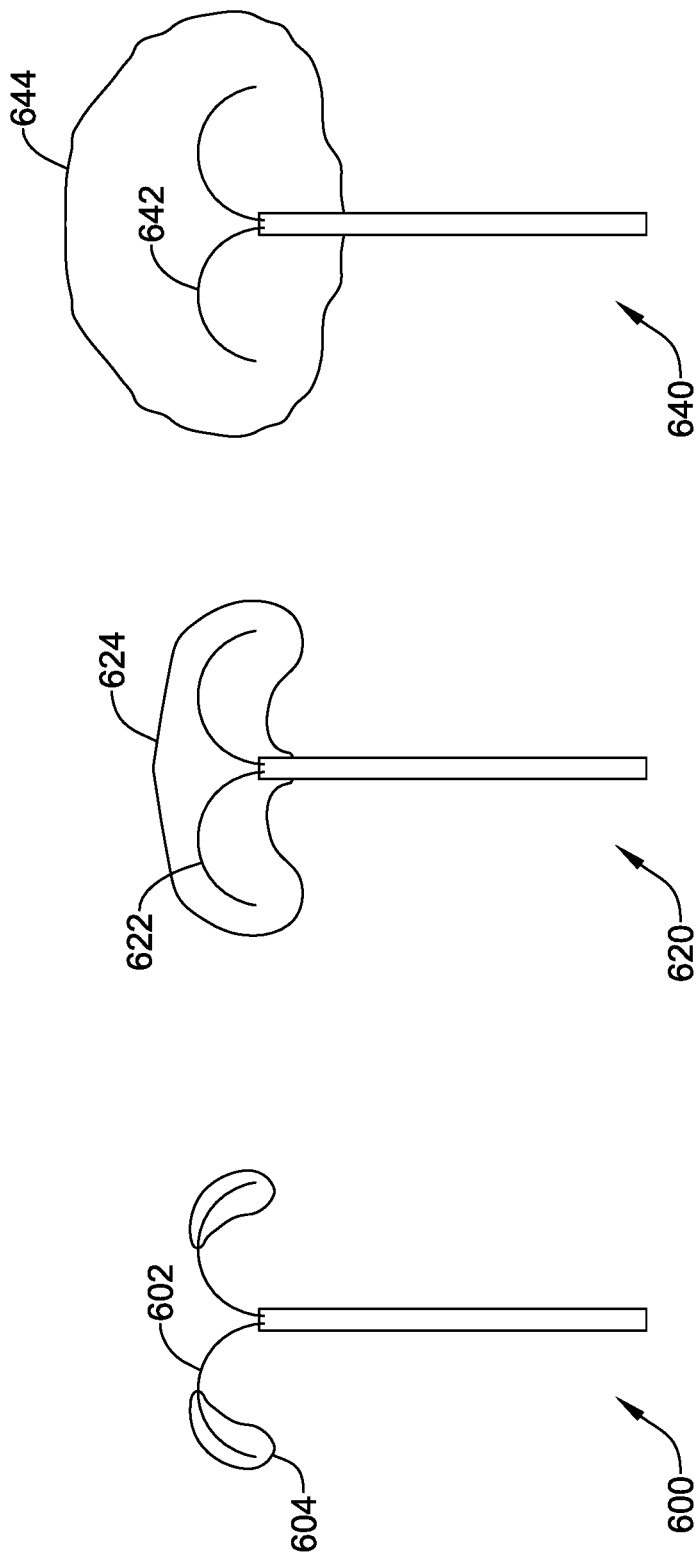

ENHANCED NEEDLE ARRAY AND THERAPIES FOR TUMOR ABLATION

CROSS REFERENCE TO RELATED APPLICATIONS

The present application claims the benefit of and priority to U.S. Provisional Patent Application No. 62/620,873, filed Jan. 23, 2018, titled ENHANCED NEEDLE ARRAY AND THERAPIES FOR TUMOR ABLATION, the disclosure of which is incorporated herein by reference.

BACKGROUND

A variety of therapy modalities have been researched and used for destruction of tumors in the body. Cryoablation and thermal ablation use cold and heat, for example, to destroy tissue. Thermal ablation can be effective and very useful, but has proven difficult to control, particularly in spatial terms. Thermal ablation is not particularly selective in terms of which tissue it will destroy, hampering post-therapy recovery as useful tissue structure such as vasculature is destroyed along with targeted tissue.

Electroporation has been used in various forms to treat targeted tissue. Electroporation operates by applying electrical pulses that cause cell membranes to alter, creating pores. Above a first threshold electrical field, the cell membranes begin to form pores. Above a second, higher threshold field, those pores can become irreversible, leading to cell death. Thus there are two forms of electroporation, reversible electroporation and irreversible electroporation (IRE). Reversible electroporation can be used in conjunction with the infusion of drugs or other agents which pass through reversibly created pores, where the infused drug/agent then causes selective cell death, however, such added agents can have systemic side effects on the patient.

New and alternative devices and methods of applying therapy are desired which can combine the beneficial uses of IRE and thermal ablation, as well as reversible electroporation.

OVERVIEW

The present inventors have recognized, among other things, that a problem to be solved is a need for new devices that provide greater physician control over the shaping and use of electrical pulses for IRE and thermal ablation. In some examples, the present invention provides devices that allow a physician to manipulate the exposed electrode surfaces on a tissue destruction apparatus. The present inventors have also recognized that it may be desirable for a physician to be able to combine IRE and one or more additional therapies such as thermal ablation and/or ablation through (or augmented by) the injection of fluids containing drugs, biologics, or other substances.

A first illustrative, non-limiting example takes the form of a system for destruction of tissue comprising a cannula having a proximal end and a distal end and containing a plurality of tissue penetrating elongate electrodes therein, the electrodes being extendible beyond the distal end of the cannula; a shaft electrode disposed near the distal end of the cannula; electrical connectors including at least one electrical connector electrically coupled to at least one of the elongate electrodes, and at least one electrical connector electrically coupled to the shaft electrode; and a sheath movable relative to the shaft electrode and adapted to control exposure of the shaft electrode to patient tissue.

Additionally or alternatively, the shaft electrode has a length, and the sheath may be moveable to control how much of the length of the shaft electrode is exposed.

Additionally or alternatively, the shaft electrode extends radially about a portion of the cannula, and the sheath may be moveable to control radial exposure of the shaft electrode.

Additionally or alternatively, the cannula may include a fluid delivery lumen and a distal portion of the cannula may comprise one or more apertures for fluid infusion. In some examples, the one or more apertures for fluid infusion are located on a first side of the cannula, and the shaft electrode is located on a second side of the cannula, such that the apertures and shaft electrode occupy opposing sides of the cannula within a single axial region of the cannula.

Additionally or alternatively, at least one of the tissue penetrating elongate electrodes may comprise a fluid delivery lumen therethrough.

Additionally or alternatively, at least one of the tissue penetrating elongate electrodes may comprise a dielectric coating on a first side of a portion thereof.

Additionally or alternatively, the shaft electrode may be disposed at a spacing distance from the distal end of the cannula, wherein the spacing distance is adjustable.

Additionally or alternatively, the shaft electrode may be cylindrical and extend the entire way around the cannula.

Additionally or alternatively, wherein the shaft electrode may extend about only a portion of the cannula.

Additionally or alternatively, the plurality of tissue penetrating electrodes may include at least a first tissue penetrating electrode having a first electrical connection and a second tissue penetrating electrode having a second electrical connection, wherein the first and second electrical connections are separately addressable.

Additionally or alternatively, the sheath may be adapted to cover a radial portion of the shaft electrode to facilitate directional control of an output electrical field between a selected one or more of the first and second tissue penetrating electrodes and a portion of the shaft electrode.

Additionally or alternatively, the plurality of tissue penetrating electrodes may include at least a first tissue penetrating electrode having a first mechanical coupling and a second tissue penetrating electrode having a second mechanical coupling, wherein the first and second mechanical couplings are separately actuatable to allow the first and second tissue penetrating electrodes to be advanced independent of one another.

A second illustrative, non-limiting example takes the form of a system for destruction of tissue comprising: a cannula having a proximal end and a distal end and containing a plurality of tissue penetrating elongate electrodes therein, the electrodes being extendible beyond the distal end of the cannula; a shaft electrode disposed near the distal end of the cannula; and a plurality of electrical connectors including at least one electrical connector electrically coupled to at least one of the elongate electrodes, and at least one electrical connector electrically coupled to the shaft electrode; wherein the shaft electrode is disposed at a spacing distance from the distal end of the cannula, wherein the spacing distance is adjustable.

Additionally or alternatively, the plurality of tissue penetrating electrodes may include at least a first tissue penetrating electrode having a first mechanical coupling and a second tissue penetrating electrode having a second mechanical coupling, wherein the first and second mechanical couplings are separately actuatable to allow the first and second tissue penetrating electrodes to be advanced independent of one another.

A third illustrative, non-limiting example takes the form of a method of ablating a tissue region using a cannula having a shaft with proximal and distal ends, and one or more tissue penetrating electrodes passing through the shaft and moveable relative to the shaft, the method comprising: inserting the cannula to place the distal end of the shaft at a desired location near a target tissue; advancing at least one of the one or more tissue penetrating electrodes beyond the distal end of the shaft to pierce tissue; delivering a first waveform adapted to cause thermal ablation in a first region relatively nearer to the at least one tissue penetrating electrode; delivering a second waveform adapted to cause irreversible electroporation in a second region relatively more distant from the at least one tissue penetrating electrode.

Additionally or alternatively to the third illustrative, non-limiting example, the shaft may have a shaft electrode thereon and the cannula comprises a sheath adapted to be moveable relative to the shaft to cover or uncover all or portions of the shaft electrode, and the method further comprises manipulating the sheath to expose a first area of the shaft electrode while the first waveform is delivered, and manipulating the sheath to expose a second area of the shaft electrode while the second waveform is delivered, wherein the first and second areas are different from one another, further wherein each of the first and second waveforms are delivered using at least one of the at least one tissue penetrating electrodes and the shaft electrode as opposing poles for an electrical output.

Additionally or alternatively to the third illustrative, non-limiting example, the shaft may comprise a fluid infusion lumen having an opening near the distal end thereof, and the method further comprises infusing a fluid through the fluid infusion lumen prior to delivering the first waveform, the fluid adapted to dampen a thermal effect of the first waveform for a first volume of tissue.

Additionally or alternatively to the third illustrative, non-limiting example, the shaft may comprise a fluid infusion lumen having an opening near the distal end thereof, and the method further comprises infusing a fluid through the fluid infusion lumen prior to delivering the first waveform, the fluid adapted to enhance a thermal effect of the first waveform for a first volume of tissue.

Additionally or alternatively to the third illustrative, non-limiting example, the shaft may comprise a fluid infusion lumen having an opening near the distal end thereof, and the method further comprises infusing a fluid through the fluid infusion lumen prior to delivering the second waveform, the fluid adapted to enhance the electrical effect of the second waveform.

Additionally or alternatively to the third illustrative, non-limiting example, the step of delivering the first waveform may be performed prior to delivering the second waveform.

Additionally or alternatively to the third illustrative, non-limiting example, the step of delivering the first waveform may be performed after delivering the second waveform.

Additionally or alternatively to the third illustrative, non-limiting example, the first and second waveforms may be each delivered repeatedly by alternating between the first and second waveforms.

Additionally or alternatively to the third illustrative, non-limiting example, the first waveform may be delivered using a first of the at least one tissue penetrating electrodes, and the second waveform may be delivered using a second of the at least one tissue penetrating electrodes.

Additionally or alternatively to the third illustrative, non-limiting example, the first waveform may be delivered repeatedly in a first therapy set, and the second waveform may be delivered repeatedly in a second waveform set.

Additionally or alternatively to the third illustrative, non-limiting example, the method may further comprise repositioning the electrodes after the first therapy set and before the second therapy set.

Additionally or alternatively to the third illustrative, non-limiting example, at least the second waveform may induce each of reversible and irreversible electroporation, and the method comprises infusing a fluid adapted to cause cell death to a region affected by the reversible electroporation.

Additionally or alternatively to the third illustrative, non-limiting example, the shaft may have a shaft electrode thereon and the cannula may comprise a sheath adapted to be moveable relative to the shaft to cover or uncover all or portions of the shaft electrode, wherein the method further comprises applying a grounding pad to the patient, wherein the first waveform is delivered using the grounding pad and at least one of the at least one tissue penetrating electrodes as the electrodes for therapy delivery, and the second waveform is delivered using the shaft electrode and at least one of the at least one tissue penetrating electrodes.

Additionally or alternatively to the third illustrative, non-limiting example, the method may further comprise manipulating the sheath relative to the shaft electrode to expose or cover the shaft electrode between delivery of the first and second waveforms.

Additionally or alternatively to the third illustrative, non-limiting example, the shaft may have a shaft electrode thereon and the cannula may comprise a sheath adapted to be moveable relative to the shaft to cover or uncover all or portions of the shaft electrode, and the method further comprises applying a grounding pad to the patient, wherein the first waveform is delivered using the shaft electrode and at least one of the at least one tissue penetrating electrodes, and the second waveform is delivered using the grounding pad and at least one of the at least one tissue penetrating electrodes as the electrodes for therapy delivery.

Additionally or alternatively to the third illustrative, non-limiting example, the method may further comprise manipulating the sheath relative to the shaft electrode to expose or cover the shaft electrode between delivery of the first and second waveforms.

A fourth illustrative, non-limiting example takes the form of a method of ablating a tissue region using a cannula having a shaft with proximal and distal ends, and one or more tissue penetrating electrodes passing through the shaft and moveable relative to the shaft, the method comprising: inserting the cannula to place the distal end of the shaft at a desired location near a target tissue; advancing at least one of the one or more tissue penetrating electrodes beyond the distal end of the shaft to pierce tissue; and delivering a waveform adapted to cause thermal ablation in a first region relatively nearer to the at least one tissue penetrating electrode and irreversible electroporation in a second region relatively more distant from the at least one tissue penetrating electrode.

Additionally or alternatively to the fourth illustrative, non-limiting example, the step of delivering a waveform induces reversible electroporation in a third region and the method may further comprise infusing a fluid adapted to cause cell death to a region affected by the reversible electroporation.

Each of these non-limiting examples can stand on its own, or can be combined in various permutations or combinations with one or more of the other examples.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 12-13 show illustrative effects of different therapy modes with different electrode configurations;

DETAILED DESCRIPTION

Figure 1:
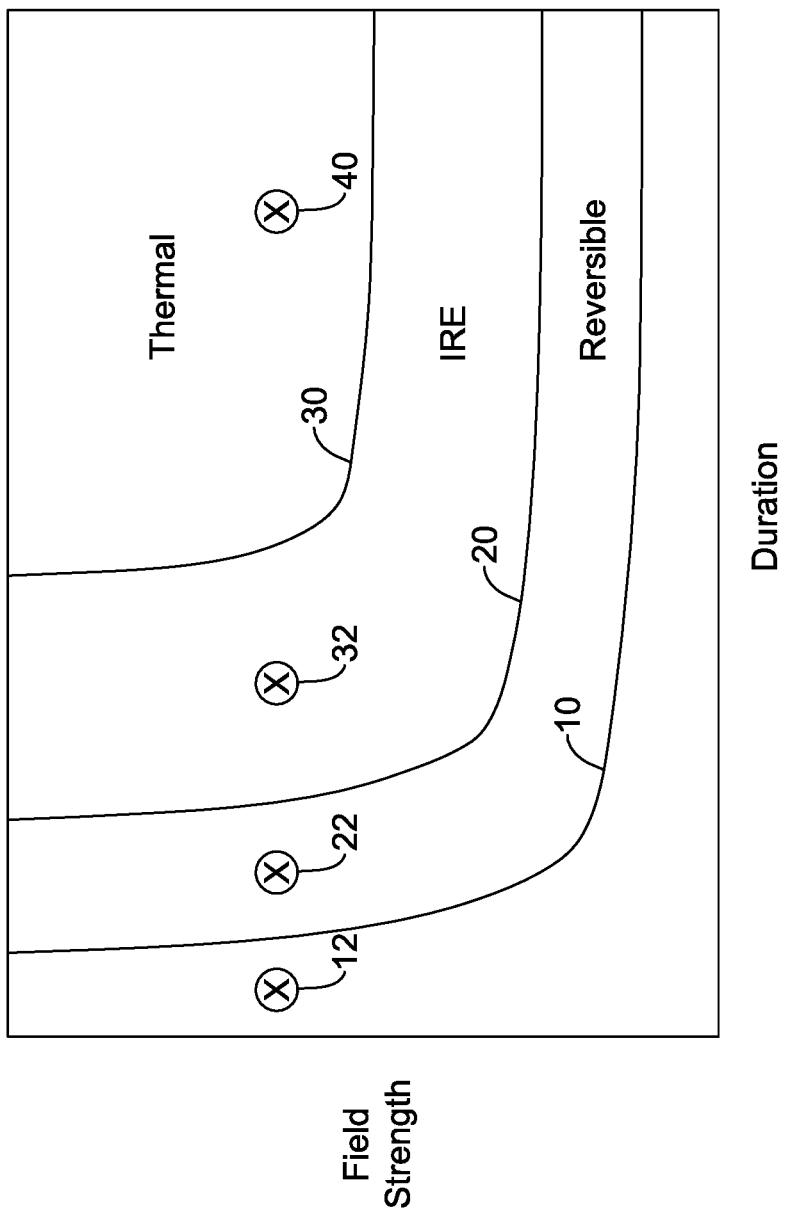
FIG. 1 shows an approximation of different therapy modalities associated with a combination of electrical field strength and pulse duration.

FIG. 1 shows an approximation of different biophysical responses dependent on the amplitude-time relationship of delivered electrical pulses. The thresholds between cellular responses (10, 20, 30) operate generally as a function of the applied field strength and pulse duration. Below a first threshold 10, no effect occurs; between the first threshold 10 and a second threshold 20, reversible electroporation occurs. Above the second threshold 20, and below a third threshold 30, primarily irreversible electroporation (IRE) occurs. Above a third threshold 30, the effects begin to be primarily thermal. Thus, for example, at a given field strength and duration there may be no effect (location 12), and extending the duration of the field application can yield reversible electroporation (location 22), irreversible electroporation (location 32), and thermal ablation (location 40).

As described in U.S. Pat. No. 6,010,613, a transmembrane potential in the range of about one volt is needed to cause reversible electroporation, however the relationship between pulse parameters such as timing and duration and the transmembrane potential required for reversible electroporation remains an actively investigated subject. The required field may vary depending on characteristics of the cells to be treated. At a macro level, reversible electroporation requires a voltage in the level of hundreds of volts per centimeter, with irreversible electroporation requiring a still higher voltage. As an example, when considering in vivo electroporation of liver tissue, the reversible electroporation threshold field strength may be about 360 V/cm, and the irreversible electroporation threshold field strength may be about 680 V/cm, as described in U.S. Pat. No. 8,048,067. Generally speaking, a plurality of individual pulses are delivered to obtain such effects across the majority of treated tissue; for example, 2, 4, 8, 16, or more pulses may be delivered.

The field for electroporation has typically been applied by delivering a series of individual pulses each having a duration in the range of tens to hundreds of microseconds. For example, U.S. Pat. No. 8,048,067 describes a series of eight 100 microsecond pulses delivered at 1 second intervals. The '067 patent describes analysis and experiments performed to illustrate that the area between lines 20 and 30 in FIG. 1 actually exists, and that a non-thermal IRE method can be achieved.

The tissue membrane does not return instantaneously, from a porated state. As a result, the application of pulses close together in time can have a cumulative effect as described, for example, in U.S. Pat. No. 8,926,606. In addition, a series of pulses can be used to first porate a cell membrane and then move large molecules through generated, reversible pores, as described in US PG Patent App. Pub No. 2007/0025919.

While U.S. Pat. No. 8,048,067 discusses performing IRE without thermal effects, and U.S. Pat. No. 8,926,606 discusses achieving IRE without delivering pulses that exceed line 20 of FIG. 1 and using cumulative effects of closely spaced pulses, the present invention in some examples is directed at the use of multiple regions of FIG. 1. For example, a single device using either one output circuit having programmable or reconfigurable features, or a single device having a plurality of output circuits tuned to different regions (in terms of voltage, pulse width, or other parameters), may be used to purposefully deliver both thermal and non-thermal ablation therapies. Tuning and tailoring the outputs, including the use of different electrode combinations and therapy parameters, may allow thermal ablation in one spatial region and IRE or other ablation in a second spatial region. Thus, some examples are directed to new and distinct devices that can be manipulated and optimized for delivering therapy within any of the regions shown in FIG. 1. Still further examples combine these concepts to provide a device suited to delivering multiple and distinct therapies such as by achieving IRE pulses in one therapy regimen with a first device configuration, and achieving thermal effects in another therapy regimen using a second device configuration. Additional combinations and details are discussed below.

Figure 2:
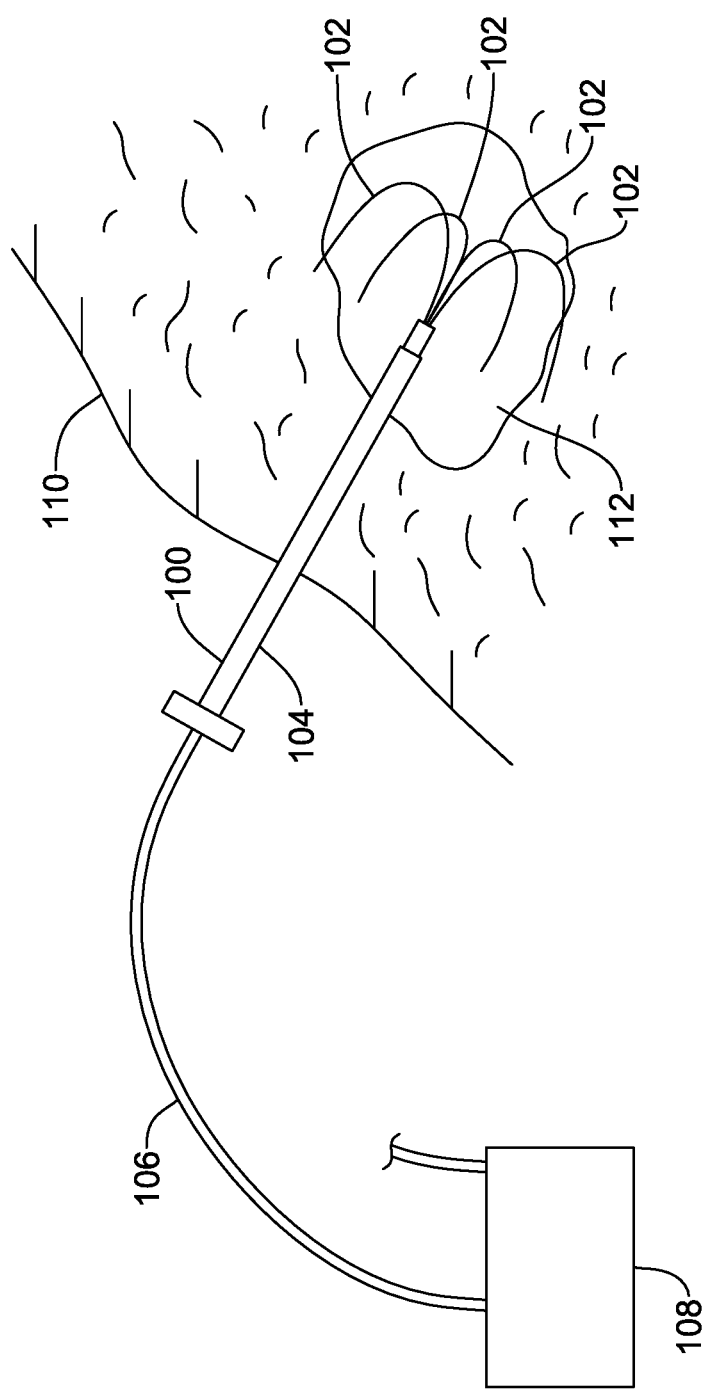
FIG. 2 shows a prior art "Leveen" needle.

FIG. 2 shows a prior art "Leveen" needle. As described in U.S. Pat. No. 5,855,576, the device comprises an insertable portion 100 having a shaft 104 that extends to a plurality of tissue piercing electrodes 102 that can be extended or retracted once a target tissue 112 of a patient 110 is accessed. The proximal end of the apparatus is coupled by an electrical connection 106 to a power supply 108, which can be used to supply RF energy. Typically the Leveen needle would be used to deliver thermal ablation to the target tissue. As described in the '576 patent, a return electrode in the form of a plate or plates may be provided on the patient's skin, a return electrode could be provided as another tissue piercing electrode, or a return electrode may be provided on the shaft 104 near its distal end, proximal of the tissue piercing electrodes 102. Enhancements on the original design can be found, for example, in U.S. Pat. No. 6,638,277, which discusses independent actuation of the tissue piercing electrodes 102, both in terms of movement of the electrodes as well as separately electrically activating individual ones of the electrodes. The U.S. Pat. Nos. 5,855,576 and 6,638,277 patents are incorporated herein by reference.

Figure 3:
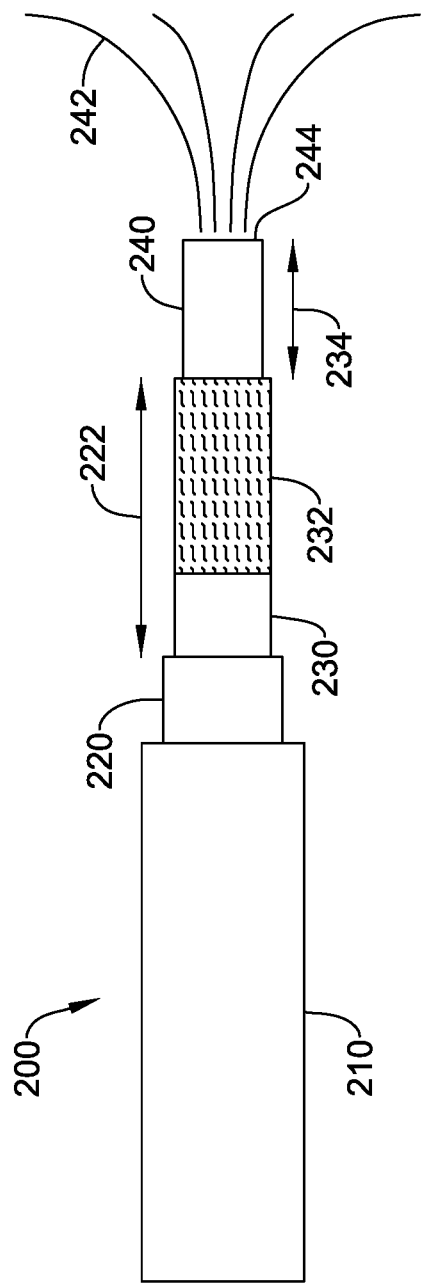
FIGS. 3-7 show illustrative example therapy apparatuses.

FIGS. 3-7 show illustrative example therapy apparatuses. Referring now to FIG. 3, a device 200 is shown having a main shaft portion 210, with a moveable insulative sheath 220 coaxially disposed therein. The sheath 220 partly surrounds an inner shaft 230 that carries a return electrode 232, which may be referred to herein also as a shaft electrode 232. The inner shaft surrounds a needle carrier 240 that has the tissue piercing electrodes 242 contained therein. The tissue piercing electrodes 242 are extendible beyond the distal end of the device 200, and particularly beyond the distal end of the inner shaft 230. Aside from the electrodes 232, 242, the remaining elements that are exposed to the patient's tissue are generally not conductive, being formed, for example, of dielectric polymers; the electrodes may be for example, titanium, stainless steel, gold, or other conductive metals, for example. Those skilled in the art will recognize various materials that may be used in addition to those noted.

In use, the position of the return electrode 232 can be adjusted relative to the distal tip 244 of the needle carrier 240 as indicated at 234, so as to affect the resulting electric field distribution and corresponding tissue response. In some examples, the distal tip 244 of the needle carrier 240 may be pointed or sharpened to allow it to pierce into the targeted tissue prior to advancement of the tissue piercing electrodes 242. The sheath 220 can be manipulated to advance or retract it relative to the return electrode 232. In this example, therefore, the return electrode 232 can be covered by the sheath 220 and thereby insulated from tissue to allow use in a unipolar mode, or may be partly covered by the sheath 220 to limit the exposed surface area of the return electrode 232. In addition, the distance between the return electrode and the distal end 244 of the needle carrier 240 may be manipulated as well.

Figure 4:
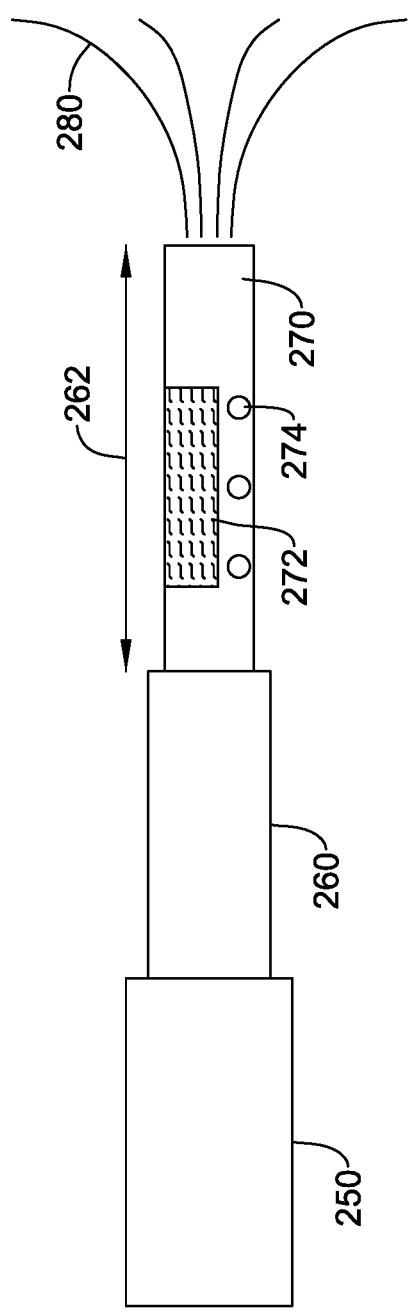

FIG. 4 shows another example. Here the device or cannula 250 includes a moveable sheath 260 that can be advanced or retracted as indicated at 262, as well as tissue piercing electrodes 280 which are again configured to be advanced and/or retracted beyond the distal end of the device or cannula 250 and in particular the needle carrier or inner shaft 270. The needle carrier or inner shaft 270 has a return electrode 272 (which may also be referred to as a shaft electrode) thereon on one side, and one or more fluid infusion apertures as shown at 274. The fluid infusion apertures 274 may be as shown, at about the same longitudinal location on the inner shaft 270 as the shaft electrode 272, or may be distal and/or proximal thereto, if desired. One or more lumens within the inner shaft 270 can be used to deliver fluid to the fluid infusion apertures 274. The shaft electrode 272 can be placed on one side of the device for use in generally single sided lesion formation, which is commonly used for example in prostate treatments where the therapy catheter is introduced next to, rather than into, the target tissue. If desired, one or more of the tissue piercing electrodes 280 may include a fluid lumen therein to allow delivery of a fluid through the tissue piercing electrodes 280. For example the tissue piercing electrodes may the take form of a hypotube.

The fluid infusion apertures may be used to deliver a fluid that enhances the electrical conductivity of the surrounding tissue in some examples. In other examples, a fluid may be infused that contains a drug, macromolecules, biologic, or other substance which will affect cell properties in one or more ways. For example, macromolecules that disrupt cellular function may be injected, with the intent being to have cells uptake the macromolecules while porated to lead to cell death. In another example, a cationic polymer may be injected, which may increase the susceptibility of the cellular membrane to poration, as described in U.S. Provisional Patent Application Ser. No. 62/585,849, titled IRREVERSIBLE ELECTROPORATION THROUGH A COMBINATION OF SUBSTANCE INJECTION AND ELECTRICAL FIELD APPLICATION.

In some examples, a fluid infusion may comprise saline, or may include dextrose, each of which will affect the conductivity of the surrounding tissue. For example, saline enhances conductivity and dextrose reduces conductivity. In another example, a fluid may be infused that will limit the scope of therapeutic effect of a thermal or IRE therapy by, for example, cooling an area of tissue or limiting current flow or electrical field propagation. For example, biocompatible mineral oil may be used, as it would limit electrical propagation by having non-conductive properties. A glycol mixture at a low concentration may be used to provide a combination of cooling and electrical resistance. In still another alternative, distilled water may be infused, reducing ion concentration, or a reverse osmosis or ion-exchange may be used. For example, a therapy apparatus may have a membrane facilitating reverse osmosis or ion exchange therethrough, reducing ion concentration and thereby increasing localized resistance. A cooling apparatus may be included, such as fluid pumping system, vaporizer or other apparatus, such as in U.S. Pat. Nos. 6,428,534 and 7,850,681, the disclosures of which are incorporated herein by reference), as cooling reduces ion mobility. At least with fluid infusion examples, the delivery of such fluids can affect the ratio of extracellular to intracellular conductivity and thereby change the local electric field across a plasma membrane.

Figure 5:
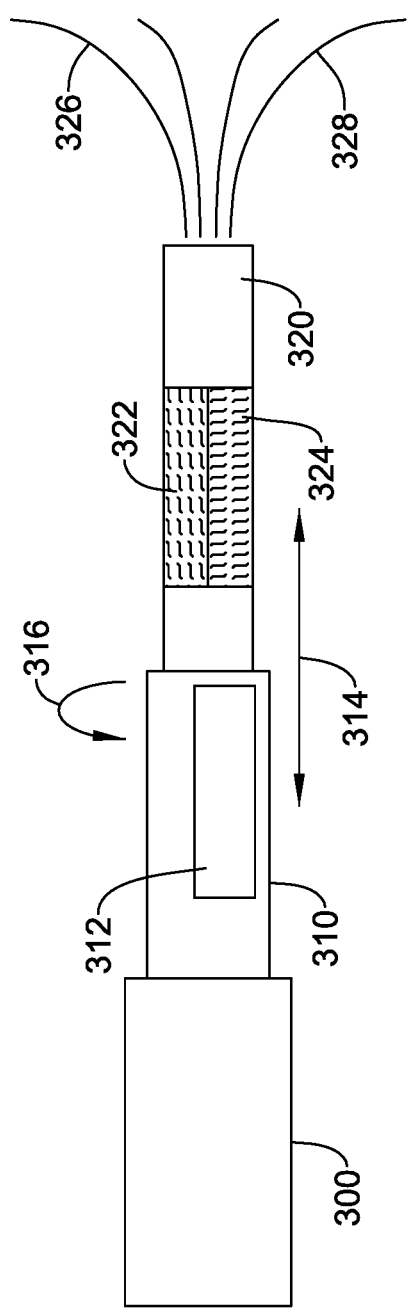

FIG. 5 shows another illustrative therapy apparatus. Here, the device or cannula 300 has a moveable sheath 310 therein having a window as indicated at 312. The sheath 310 in this example can be moved longitudinally 314 as well as rotated 316 over the inner shaft 320 having electrodes 322, 324 thereon, where the electrodes 322, 324 may be separately addressable if desired. Tissue penetrating electrodes 326, 328 may again be configured to be advanced or retracted, individually or as a group, as desired, and may also be individually addressable electrodes for the device. Thus, for example, the apparatus of FIG. 5 may allow various combinations of electrodes for therapy delivery such as:

Between electrodes 322 and 324
Between electrode 322 and either of electrodes 326, 328
Between electrode 324 and either of electrodes 326, 328
Between electrodes 326 and 328
Between electrodes 322/324 held electrically in common and electrodes 326/328 also electrically in common
Using only a portion of electrode 322, 324, or the union of electrodes 322, 324, as covered at least partly by sheath 312, and one, the other, or both of electrodes 326, 328

For example, during a first therapy application, a union of the piercing electrodes 326, 328 may serve as a pole opposed to a union of electrodes 322, 324, delivering an IRE field in a series of pulses (such as, for example, 8 pulses of 100 microsecond duration at 800 volts per centimeter delivered at about 1 Hz), followed by a second therapy application of thermal ablation output directed to the inner shaft 320 using electrodes 322, 324 as opposing poles (for example, 8 pulses of 10 millisecond duration at 800 volts per centimeter delivered at about 10 Hz). Other pairings and sequences may be used.

Figure 6:
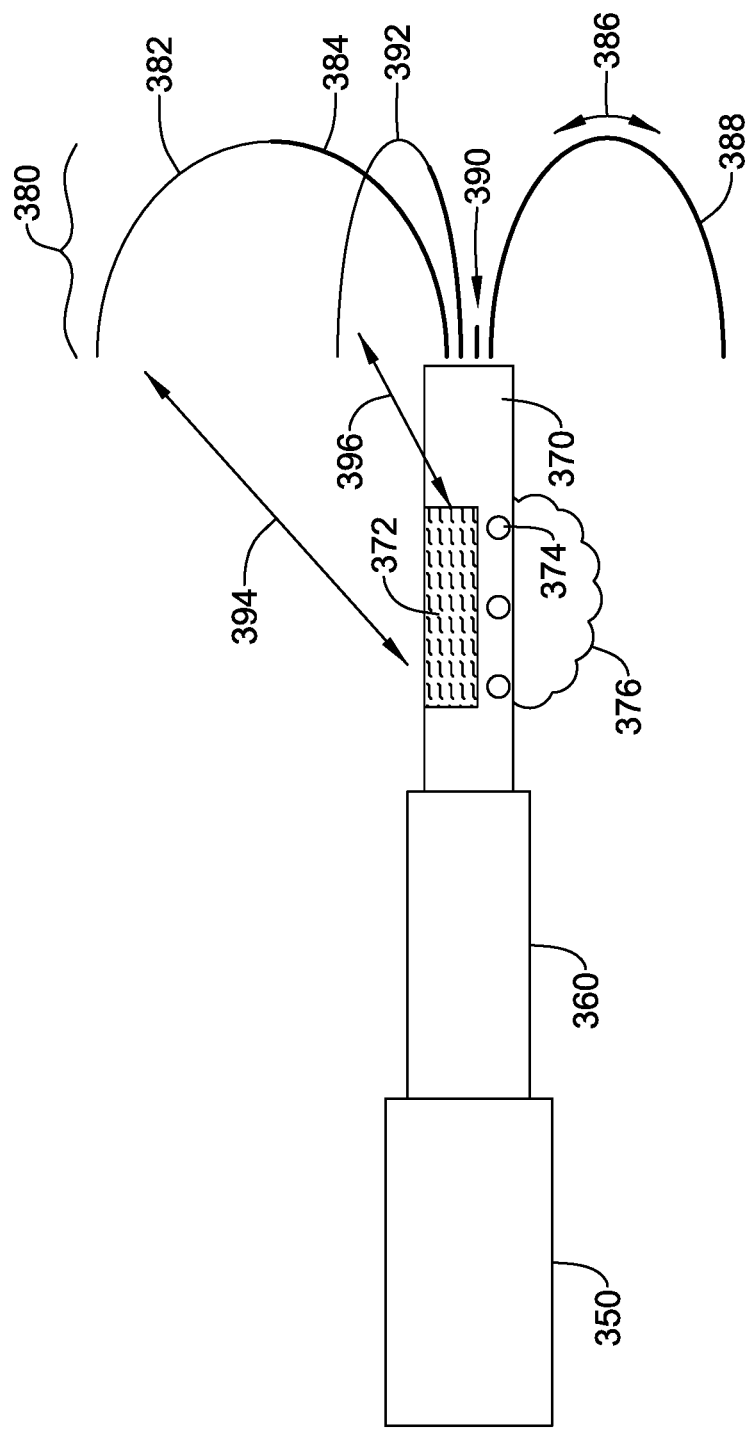

Turning now to FIG. 6, another illustrative therapy apparatus is shown. Here, the device or cannula 350 has a sheath 360 that may be manipulated relative to the inner shaft 370. The inner shaft 370 carries a shaft electrode at 372 and has fluid infusion apertures 374 that can be used to inject fluid 376. In this example, the tissue piercing electrode array 380 (which may be advanced or retracted individually or as a group, and which may be electrically addressed individually or in pairs, groups, subgroups or as an entire array) is further tailored to allow manipulation of electrode surface area. For example, tissue piercing electrode 382 has a retractable insulative sheath 384 thereon, as does electrode 392. One of the tissue piercing electrodes has a sheath extending over its entire length as indicated at 388, with the sheath 388 retractable as indicated at 386. Another of the tissue piercing electrodes is itself retracted as shown at 390. The ability to separately address and control the exposed surface area of at least some of the tissue piercing electrodes facilitates greater physician control. Now, for example, individual addressing allows separate field definition as indicated at 394 and 396, allowing greater targeting of the therapy field. In an example, the targeted and individualized fields 394, 396 may be used to deliver thermal ablation in a locally controlled space, while IRE is delivered in a therapy regimen that uses more of the tissue penetrating electrodes ganged together, for example. In this way, the thermal ablation can be targeted in areas where sensitive tissue is not present (such as vascular tissue), while IRE can be used more broadly to allow more selective killing of cells, if desired.

Figure 7:
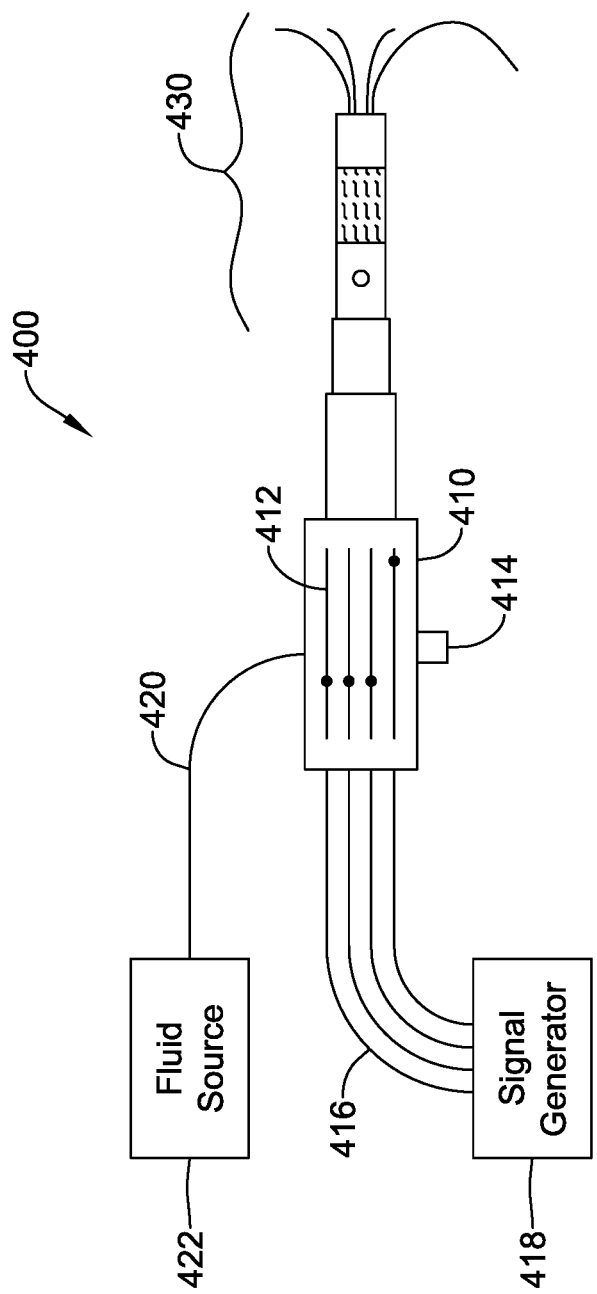
Figure 8:
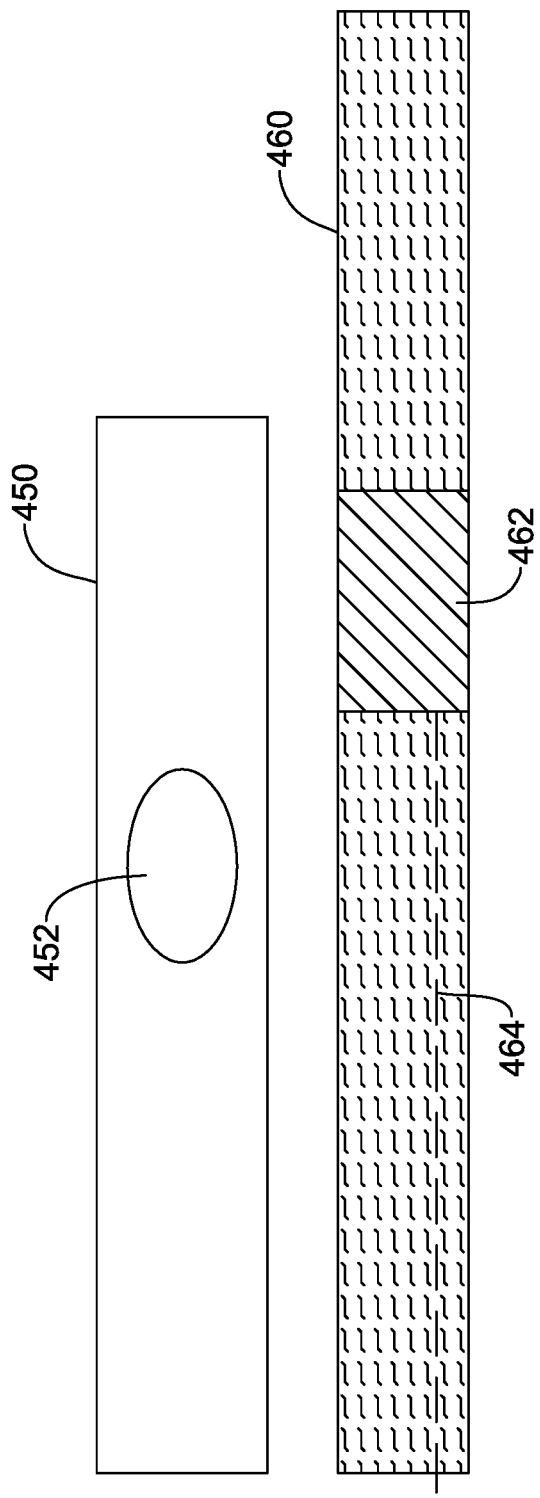
FIGS. 8-11 show an illustrative therapy apparatus with manipulation of an electrode.

FIG. 7 shows an illustrative system. The system 400 includes a therapy device 410 having a relatively complex handle structure including individual actuators 410 for manipulating the tissue piercing electrodes (individually, as groups, or as the entire array) at the distal tip of the apparatus, and a separate actuator 414 for controlling a sheath that selectively limits the exposed surface area of the return electrode. Electrical cord 416 couples to a signal generator 418, while a fluid coupling 420 is linked to a fluid source 422. The distal portion of the therapy device 410 is shown at 430 and may incorporate any of the designs in FIGS. 3-6, above, or FIGS. 8-11, below.

Figure 9:
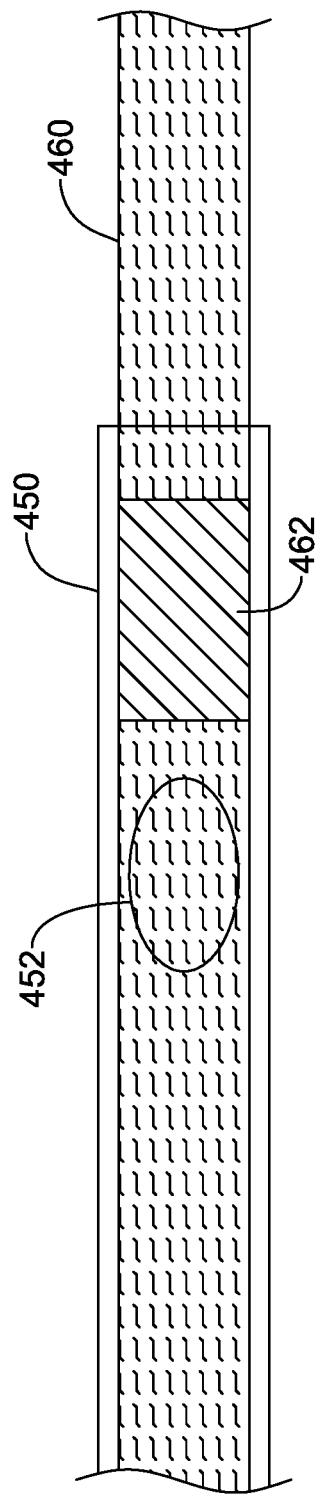
Figure 10:
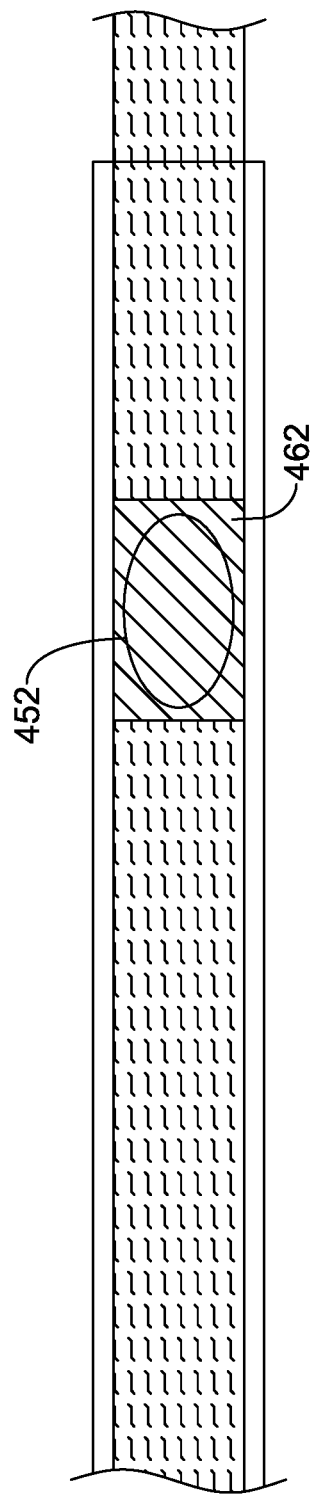
Figure 11:
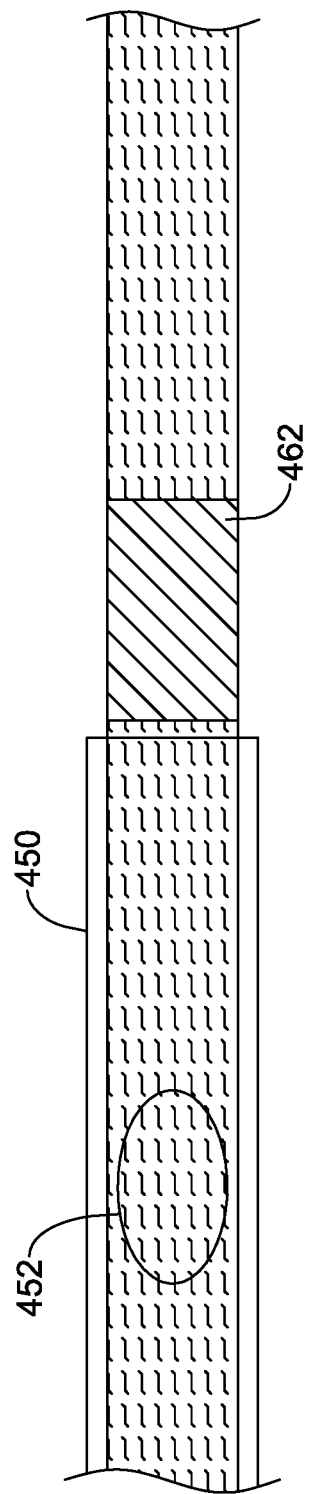

FIGS. 8-11 show an illustrative therapy apparatus with manipulation of an electrode. A sheath 450 is shown having a window at 452. The sheath may be, for example, a 0.005 inch polyimide tube, though any design or material may be used instead of polyimide of such thickness; other insulative polymers may be used, for example. The inner shaft 460 carries shaft electrode 462. The shaft electrode may be, for example, a titanium or medical grade stainless steel element, and may be a ring electrode or a directional electrode as shown in examples above. A conductor 464, such as a stainless steel conductor, can be provided through shaft 460 which may be, for example, a multi-lumen tube of any suitable material such as polyimide, poly-ether block amide, or other suitable material. In one configuration, as shown in FIG. 9, the sheath 450 may completely cover the electrode 462 by having the window 452 proximal of the electrode 462. Advancing the sheath 450 as shown in FIG. 10 allows a selected and reduced area of the electrode 462 to be exposed through window 452. Retracting the sheath 450 as shown in FIG. 11 allows the entire electrode 462 to be exposed.

Figure 12:
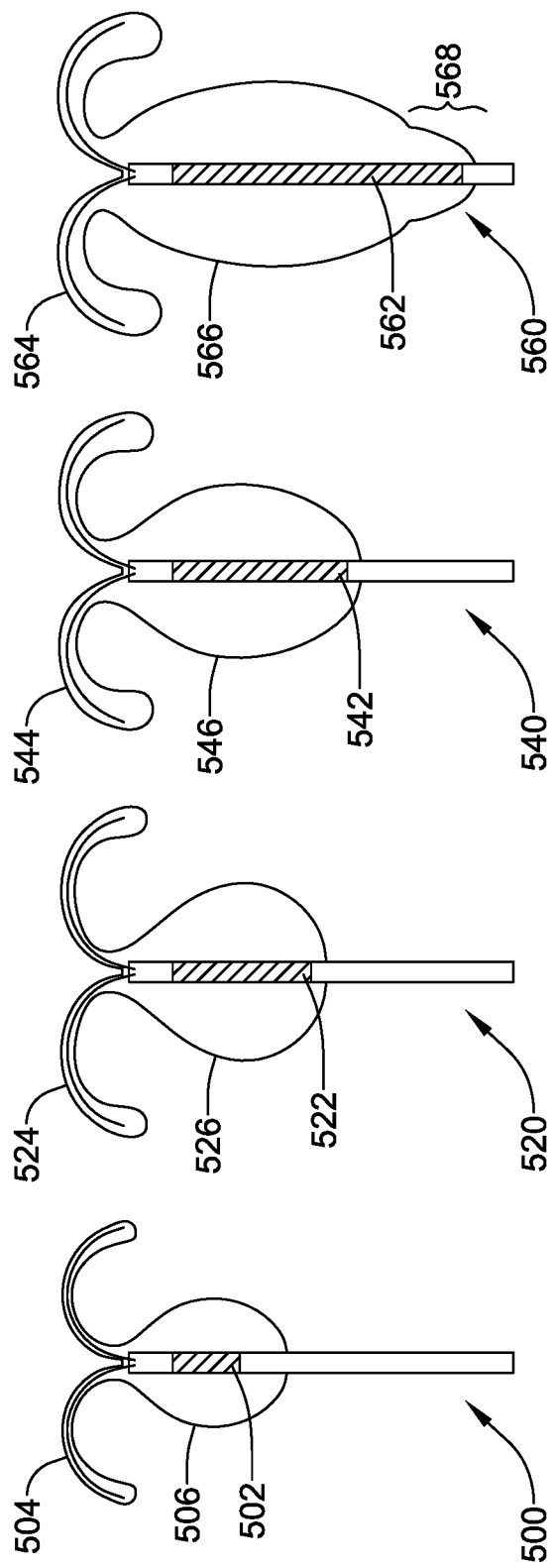

FIGS. 12-13 show illustrative effects of different therapy modes with different electrode configurations. FIG. 12 shows variation in IRE field strength with variation of shaft electrode length, using a homogenous medium model. A first example at 500 applies a 3000 volt output between a 2.5 mm shaft electrode 502 and tissue piercing electrodes 504, with the boundaries of the IRE field shown at 506. To ensure reliable IRE in the field boundary 506, in application, the output may be delivered for example as a series of 4 to 20 pulses (or more) with durations in the 0.1 to 100 microsecond range (or more) at a frequency of 1 to 100 Hz (or more or less), for example, 8 to 10 pulses of 5 microsecond duration at 10 Hz may be delivered. Using the same output voltage, a second example at 520 assumes a 5 mm shaft electrode length 522. The IRE field boundary 526 closely envelopes the tissue piercing electrodes and can be seen to have widened and lengthened about the shaft electrode 522. Extending the shaft electrode 542 length to 10 mm, as shown at 540, again elongates the boundaries of the IRE field boundary 546; it can be seen also that the field span surrounding the tissue piercing electrodes 544 becomes larger as well. Again extending the shaft electrode 562 length to 15 mm changes the shape of the IRE field boundary 566, adding still further to the margin around the tissue piercing electrodes 564, but achieving a field that narrows near the proximal end of the shaft electrode 562, as seen at 568.

FIG. 13 shows thermal ablation boundaries using a monopolar configuration. Here, a return plate electrode (not shown) is placed on the skin of the patient, typically using a hydrogel or the like to reduce tissue/electrode impedance, as the therapy device is used to deliver output therapy. As shown at 600, at a relatively lower voltage (such as 2000 volts) the thermal ablation boundaries 604 are generally limited to the region of the tissue piercing electrodes. With increased voltage, as shown at 620 and 640, the thermal ablation region expands quickly to develop a volume around the tissue penetrating electrodes 622, 642.

The ability to manipulate the shape and volume of treatment effectiveness can be used in a variety of ways. In some examples, the shaft electrode size may be varied while a plurality of IRE treatments take place, wherein the individual IRE treatments comprise a plurality of applied pulses delivered as a set of therapy pulses, and wherein the shaft electrode size and usage is changed from one set to the next as by, for example, exposing more or less of the shaft electrode from one set to the next, or by switching from a monopolar to bipolar treatment mode by enabling or disabling the shaft electrode. For example, thermal ablation modalities can be difficult to control due to heat sink effects of blood flow in nearby vasculature and/or the treatment device itself. In the prior art, tract seeding can be prevented by applying ablation therapy during retraction of the device to cause a thin layer of tissue necrosis along the tract. Application of IRE pulses in sets before or after the thermal treatment may target not only the tissue adjacent to the electrodes themselves, but also tissue that is located outside of the thermal treatment region between two electrodes.

In some examples, IRE and thermal treatments are combined into one overall therapy regimen as by, for example, alternating between pulses of longer duration (which generate thermal effects) and shorter duration (which generate IRE-type effects) within a therapy pulse set. In another example, an IRE output is generated after a thermal output and before adjustment of electrode position to target a different area of the anatomy; for example, a sequence of thermal output and IRE output may be followed by extending or retracting an electrode or insulator over an electrode, with the thermal output used to create larger volume effects and the IRE output used to eliminate possible tract seeding.

In another example, IRE is used before thermal output. IRE can reduce impedance in affected tissue. By first reducing impedance, the thermal output of a subsequent stage can generate a greater quantity of thermal affect with reduced voltage output, as the lowered impedance allows higher current at a given voltage, where it is recognized that the square of the current yields the heating effect of a given therapy.

Figure 14A:
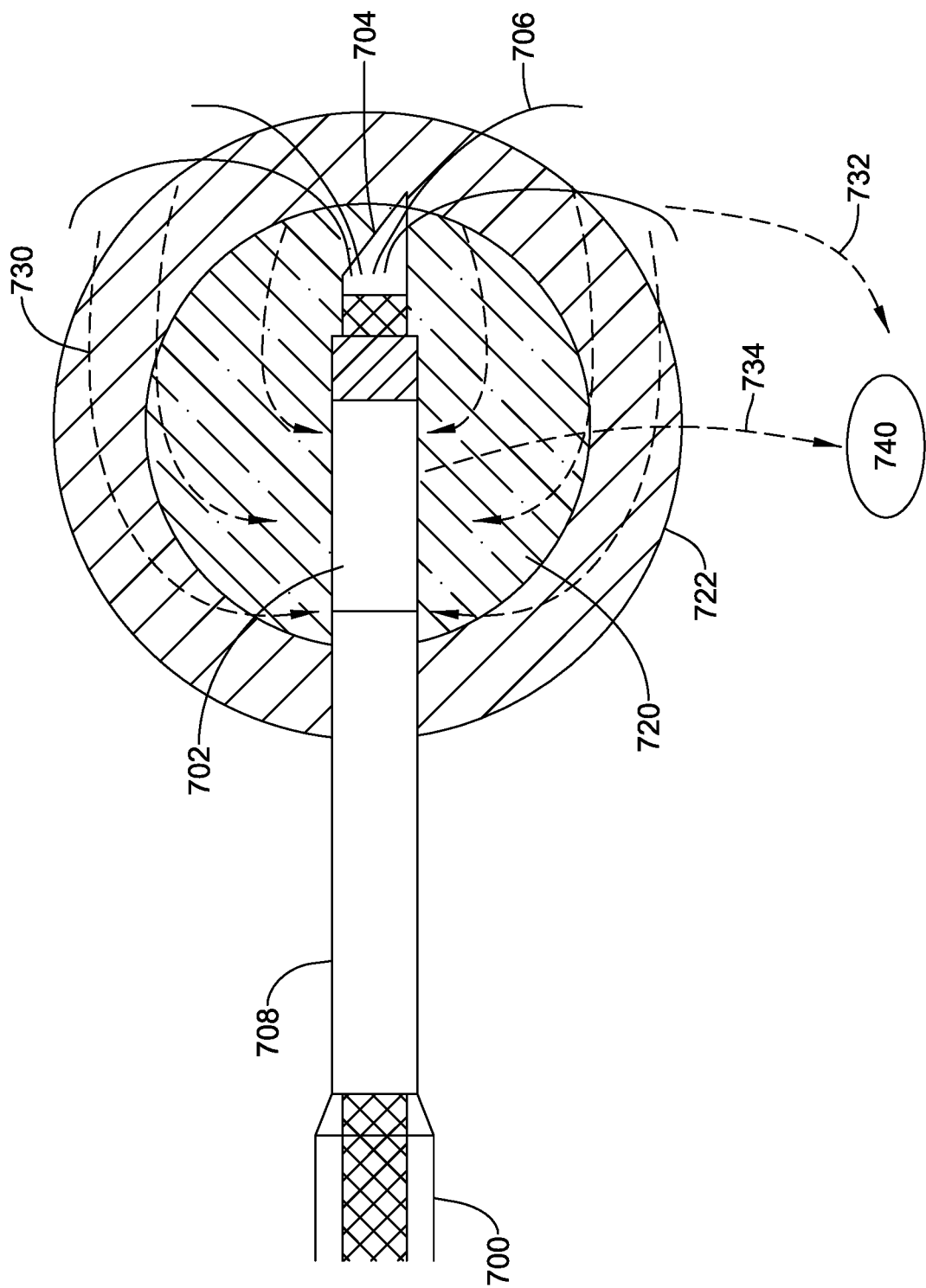
FIGS. 14A-B show a tumor being treated by an illustrative device.
Figure 14B:
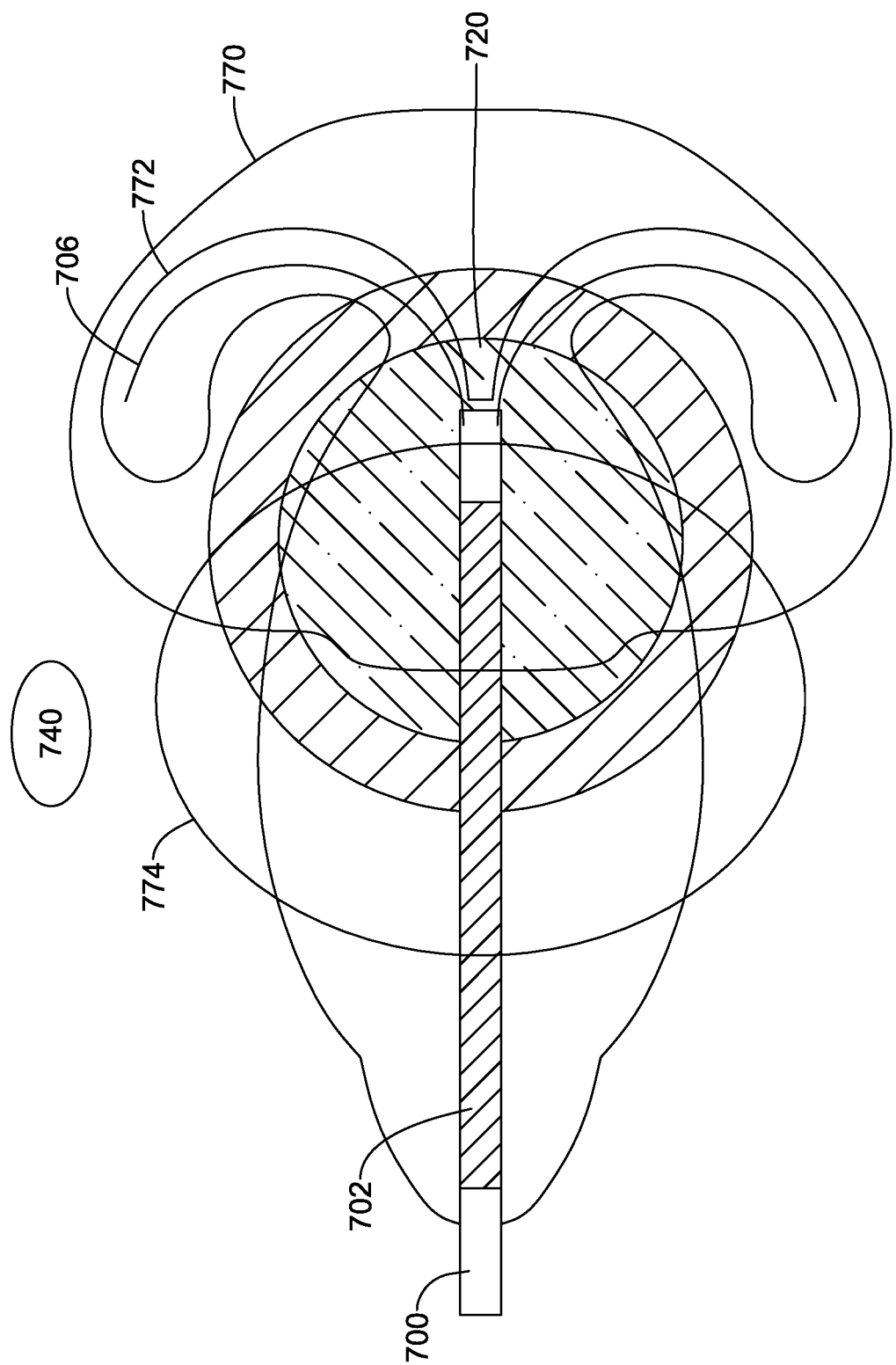

FIGS. 14A-B shows a tumor being treated by an illustrative device. In FIG. 14A, a therapy device or cannula 700 has been inserted into a patient's tissue. A shaft electrode is shown at 702, with a moveable sheath 708 on the shaft as well to adjust the area of the electrode 702 that is exposed to patient tissue.

A distal tip 704 of the cannula 700 has an angled or pointed end to allow passage through the patient tissue. In some examples the distal tip 704 is relatively sharp to allow it to pierce through tissue; such an example is shown in FIG. 14A where the distal tip 704 has been used to pierce a tumor 720 and surrounding lesion 722. In other examples the distal tip 704 may be blunted to allow atraumatic passage through a body lumen such as a biliary duct, lymph vessel or duct, urethra, mammary duct, digestive passageway, blood vessel, or other body passageway, as the case may be. The distal tip 704 may be partly blunted to allow its use to separate body tissue layers as it passes, for example, alongside the outer capsule of a body organ such as the liver or kidney.

A plurality of tissue piercing electrodes or needle electrodes are shown at 706. As can be seen, the cannula is inserted 700 far enough into the tumor to place the shaft electrode at least partly in the tumor, and the needle electrodes extend beyond the tumor and lesion. Tract seeding in this example may occur if abnormal cells from the tumor 720 stick to the needle electrodes 706 as they pass out through the lesion and into surrounding normal tissue, as well as by cells sticking to the main body of the cannula 700 such as sheath 708 and shaft electrode 702 during removal or repositioning maneuvers. In either event, the abnormal cells may be transported out of the tumor into surrounding tissue, and so an ablation or cell destruction therapy that destroys such cells in addition to the cells of the tumor 720 and surrounding lesion 722 is desirable.

In an example, a plurality of distinct treatment steps take place using differing parameters and electrodes to account for both the extent of the tumor 720 and any potential tract seeding. For example, currents 730 may be generated in a bipolar treatment stage or stages between one or more of the tissue piercing or needle electrodes 706 and the shaft electrode 702. Currents 732 may also be generated in one or more monopolar treatment stages between an external return electrode 740 and one or more of the needle electrodes 706. Currents 734 may be generated in one or more monopolar stages using the shaft electrode 702 and the external return electrode 740. The external return electrode 740 may be, for example, a grounding pad. The grounding pad or external return electrode 740 may be placed in different positions for different steps, to direct the electrical field in different directions, if desired.

FIG. 14B illustrates results of several therapy steps using distinct therapy modalities. For example, a first lesion field is generated at 770 by the use of a monopolar thermal or IRE therapy delivery using the needle electrodes 706 and an external return electrode 740. A second lesion field is generated at 772 by the use of a bipolar IRE or thermal therapy using most or all of the shaft electrode 702 as one pole and one or more of the needle electrodes 706 as opposing pole(s). A third lesion field is generated at 774 using a monopolar IRE or thermal therapy delivered using a portion of the shaft electrode 702 (for example, a lesser extent of the shaft electrode 702 may be exposed during such delivery than is shown in FIG. 14B) and an external return electrode 740. Depending on the size and shape of the tumor 720, only two such fields may be generated in some examples.

The present invention encompasses each combination of the two monopolar and bipolar therapy modes, in either IRE or thermal formats, in any desired order. The skilled person can readily generate the complete matrix. For purposes of illustration, however, following are some approaches that may be used in some specific examples:

| First Step/Type | Second Step/Type | Third Step/Type |
|---|---|---|
| 772/IRE | 770/Thermal | (none) |
| 770/Thermal | 772/IRE | (none) |
| 772/IRE | 770/Thermal | 774/Thermal |

For purposes of this illustration, the "IRE" therapy steps may have thermal effects as well, but predominantly use IRE to cause cell death; likewise, the predominant mode of cell death for the "Thermal" therapy steps will be thermal though IRE may occur in some cells as well. Factors that may differentiate Thermal from IRE therapy may include duty cycle and field strength or amplitude. Determination of whether thermal or IRE therapy has been effective can be determined through staining using immune-histo-chemical assays, which will illustrate differentiation between tissue regions subject to different types of cell death. For example, immunological response to IRE-cause cell death is distinguishable from that for thermally destroyed cells; cells that survive and/or are only subject to reversible electroporation will further show a demarcation. If desired, an additional therapy mode may comprise placing the shaft electrode 702 (or a portion thereof) electrically in common with one or more of the needle electrodes in a monopolar therapy mode, whether for IRE or thermal ablation.

In some examples a monopolar therapy mode is used for thermal ablation using a lower voltage gradient, and a bipolar therapy mode is used for IRE using a higher voltage gradient. For example, two electrodes 2.5 cm apart can use a 2000 volt output to exceed 650 V/cm field for IRE, while two electrodes 10 cm apart using 1000 volt output will yield a 100 V/cm field, which is sufficient to attain thermal effects if using longer pulse widths and/or a higher duty cycle, with the combination reducing damage or excitation on distant muscle or nerve fibers of the patient in either case. In this example, the pulse-duration and field strength relationship with thermal damage and irreversible electroporation induction is harnessed to produce a therapeutic effect with desirable damage modes.

As can be seen in FIG. 14B, while none of the individual therapy steps completely encompasses the tumor 720, the combination of modes and therapy steps captures the entire tumor as well as a margin about the tumor 720, while also addressing the possibility of tract seeding. The use of IRE in addition to thermal ablation also addresses tract seeding that could otherwise be facilitated by localized heat sink effects of the apparatus itself.

Figure 15:
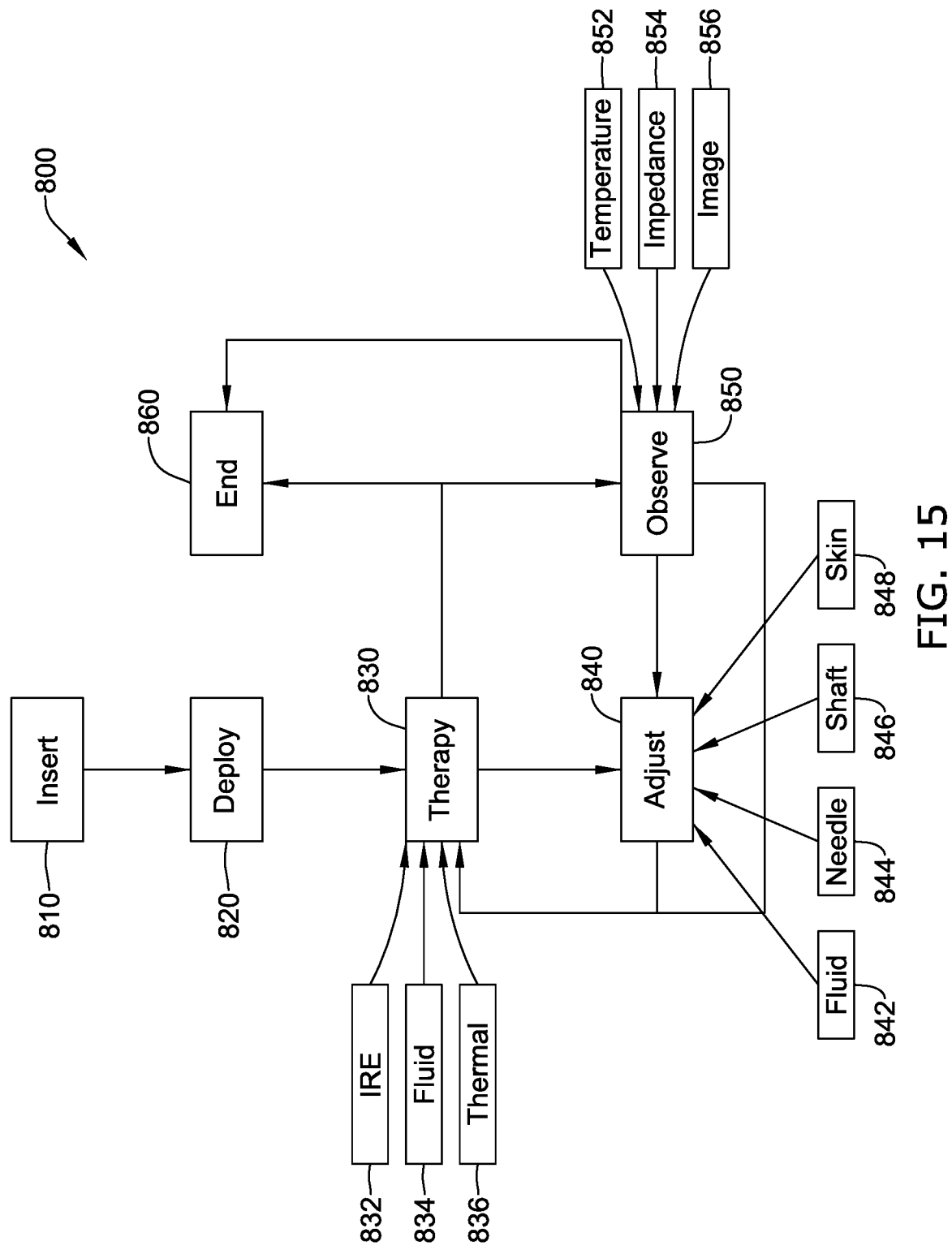
FIG. 15 is a block flow diagram illustrating various examples.

FIG. 15 is a block flow diagram illustrating various examples. The overall method 800 may be subject to a number of repetitions, both internally within the method and as separate steps in a procedure to treat a patient. A therapy device is inserted at 810. Insertion 810 may make use of an existing lumen or channel of the patient (such as using a blood vessel or other duct/vessel in the patient) or may comprise piercing tissue with an instrument designed for such piercing. Once inserted to a location that is desirable, the treatment apparatus may deploy one or more electrodes, as indicated at 820. In some example, tissue piercing electrodes, such as in the modified Leveen-style devices shown above, may be extended out of internal lumens of the therapy device to pierce tissue or otherwise position electrodes for use. A therapy is then delivered, as indicated at 830. The therapy may be, for example, an IRE therapy 832 in which monophasic or biphasic (or triphasic or other multiphasic) electrical output is generated with relatively high amplitudes (yielding fields of over 600 V/cm, for example) and short pulse widths (for example in the range of 0.1 to 100 microseconds) at a relatively lower duty cycle (such as 1 to 100 Hz—such as a duty cycle of less than 0.1%), which may avoid thermal heating to yield predominantly IRE therapy. The therapy may include injection of a fluid to enhance or modify effectiveness or spatial effects of an applied electrical therapy, or may instead be injection of an ablative fluid such as a fluid having limited caustic effects, or cooling or heating effects, as indicated at 834. The therapy may be a thermal treatment, which may incorporate somewhat lower pulse amplitudes (fields of less than 600 V/cm, for example) at longer pulse widths (for example, 10 microseconds to 100 milliseconds) at a relatively higher duty cycle (such as by application of the pulses at a frequency of 10 Hz to 100 kHz, in some examples to yield a duty cycle of greater than 0.1%). For example, saline may be injected to reduce local tissue impedance, increasing current flow for a given output voltage, such that both an electrical output (832/836) is delivered and the fluid (834). Some examples may use both IRE 832 and thermal ablation 836 from a single output waveform by increasing pulse width and/or the duty cycle of IRE outputs to cause thermal effects.

Within the illustrative example, after a therapy delivery at 830, the system proceeds to make an adjustment as indicated at 840 and then cycles back to the therapy step. For example, an adjustment may include the injection of fluid 842, selecting, deselecting, moving or modifying the exposed surface area of a needle electrode 844, adjusting the position or exposed surface area of a shaft electrode 846, or moving, adding or removing a cutaneous or skin electrode 848. In an illustration, a therapy may be delivered at 830 as a monopolar thermal ablation step 836, an adjustment may be made at 840 by exposing a shaft electrode 846 and removing or deselecting a skin electrode 848, and then delivering therapy again at 830, this time using a bipolar IRE output with shaft and needle electrodes.

In some examples a set quantity of therapy steps and adjustments 830/840 may be performed and the method ends by exiting the loop 830/840, proceeding to the end block 860. In other examples, after one or more therapy steps 830, the method engages an observation step 850, in which one or more observable features are quantities or checked to determine progress or status of the therapy. For example, block 850 may refer to temperature 852, impedance 854, and/or an imaging modality 856 such as a CT image. In some examples, impedance 854 may be checked between any selected pair of electrodes such as between needle electrodes, between a needle electrode and a shaft electrode, between a needle electrode and a surface electrode, or between a probe electrode and an electrode of the therapy apparatus, or between two probe electrodes. It should be understood that as therapy progresses, cell death may occur, releasing intercellular fluid into the extracellular matrix and reducing impedance as cell death occurs, making impedance 854 a useful observation. Also, as therapy progresses, temperature 852 may be checked to ensure that temperatures as measured using, for example a temperature sensor on the therapy apparatus or a temperature sensor on a separate probe, is in a desired range. For example, as cell death occurs, local temperature may increase more greatly as local impedance drops and current flows increase at a given voltage, making temperature a useful measure of status. An image 856 may be used as well to determine the status of a tumor or lesion. After observation 850, an adjustment 840 may be made if desired or therapy 830 may resume. If observation 850 shows satisfactory completion of treatment, the method may go to the end block 860 if desired.

In one example, several iterations of thermal therapy 830/836 may be performed, with observation 850 used to determine when the thermal therapy is sufficiently completed, and then an additional therapy may be delivered as an IRE therapy 830/832 to limit the possibility of tract seeding. Several additional examples of therapy sequences follow in FIGS. 16-20.

Figure 16:
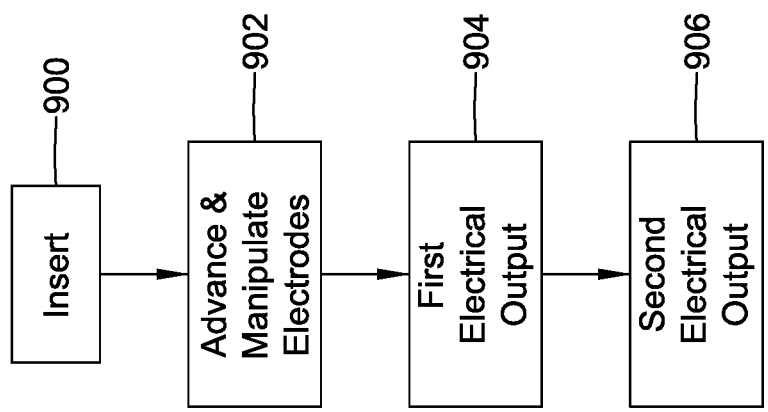
FIGS. 16-20 show a number of therapy sequences.

FIG. 16 shows one example. A therapy apparatus is inserted to a desired location at 900. Electrodes are advanced and manipulated to desired positions relative to a tumor or other target tissue, such as by establishing a perimeter near or around the target tissue, as indicated at 902. A first electrical output is provided as a first therapy step at 904, such as by delivering IRE, thermal, or an output tailored to generate a combination thereof. A second electrical output is provided as a second therapy step at 906, such as by delivering IRE, thermal, or an output tailored to generate a combination thereof. For example, an IRE therapy may be delivered at 904 and a thermal therapy at 906, or the other way around.

The method of FIG. 16, as well as any other of the examples herein, may be further combined with additional therapy elements, such as for example, the delivery of a laser ablation (by, for example, inserting a separate optical instrument or including one or more optical fibers in a therapy apparatus similar to those shown above). For example, an optical therapy apparatus may be inserted and used to perform laser-based ablation, with IRE then delivered via electrodes on the laser apparatus to mitigate tract seeding. Ultrasound or other vibrational therapy may be added as well. For example, rather than an electrical therapy as the "thermal" therapy, followed by IRE to deal with tract seeding possibilities, an ultrasound instrument may be provided and used in a first step, with electrodes provided thereon to allow use of IRE to complete the procedure prior to withdrawal of the ultrasound instrument. Thus for each of the ultrasound and laser examples, block 904 may instead be treated as deliver first therapy, where the first therapy is ultrasound or laser therapy, followed by the electrical output at 906.

Figure 17:
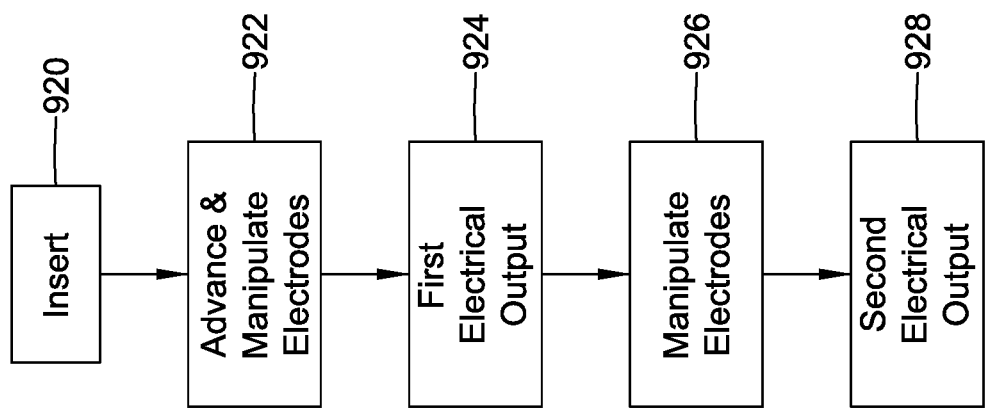

FIG. 17 shows another example. Again, a therapy apparatus is inserted 920 and electrodes thereof may be advanced and/or manipulated into a desired use configuration. A first output, which may be electrical as indicated at 924, is delivered. The electrodes are then manipulated as indicated at 926 by, for example, selecting, deselecting, moving, or adjusting the exposed surface area thereof. A second output, which may be electrical, is then delivered as indicated at 928. As with FIG. 16, the first or second outputs may be IRE, thermal, or a combination thereof.

Figure 18:
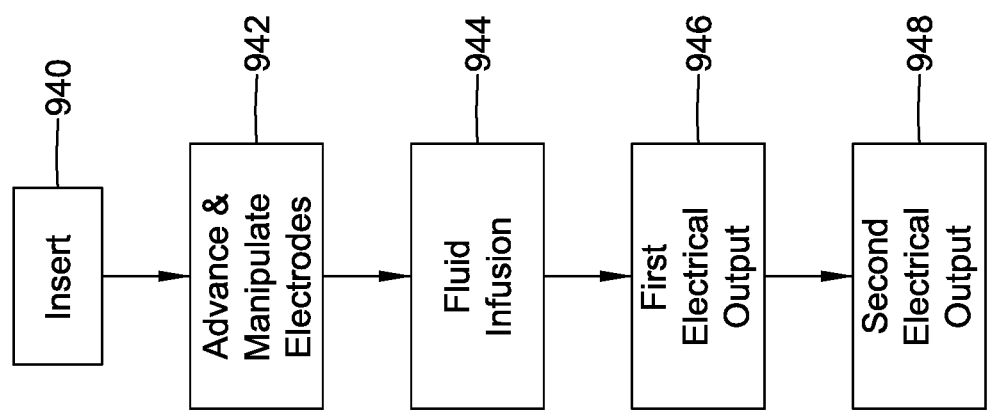

FIG. 18 shows another example. Here, a therapy apparatus is inserted 940 and electrodes thereof may be advanced and/or manipulated into a desired use configuration 942. A fluid is then infused, as indicated at 944. The fluid may be provided to enhance, augment, limit or otherwise affect the subsequent therapy steps. A first output, which may be electrical as indicated at 946 is delivered, and a second output, which may also be electrical as indicated at 948, is then delivered. The therapy outputs, if electrical, may be IRE, thermal, or a combination thereof. In the example, the therapy outputs are different from one another in one or more respects such as by having one adapted to predominantly thermal effects, while the other is tailored to predominantly IRE effects.

Figure 19:
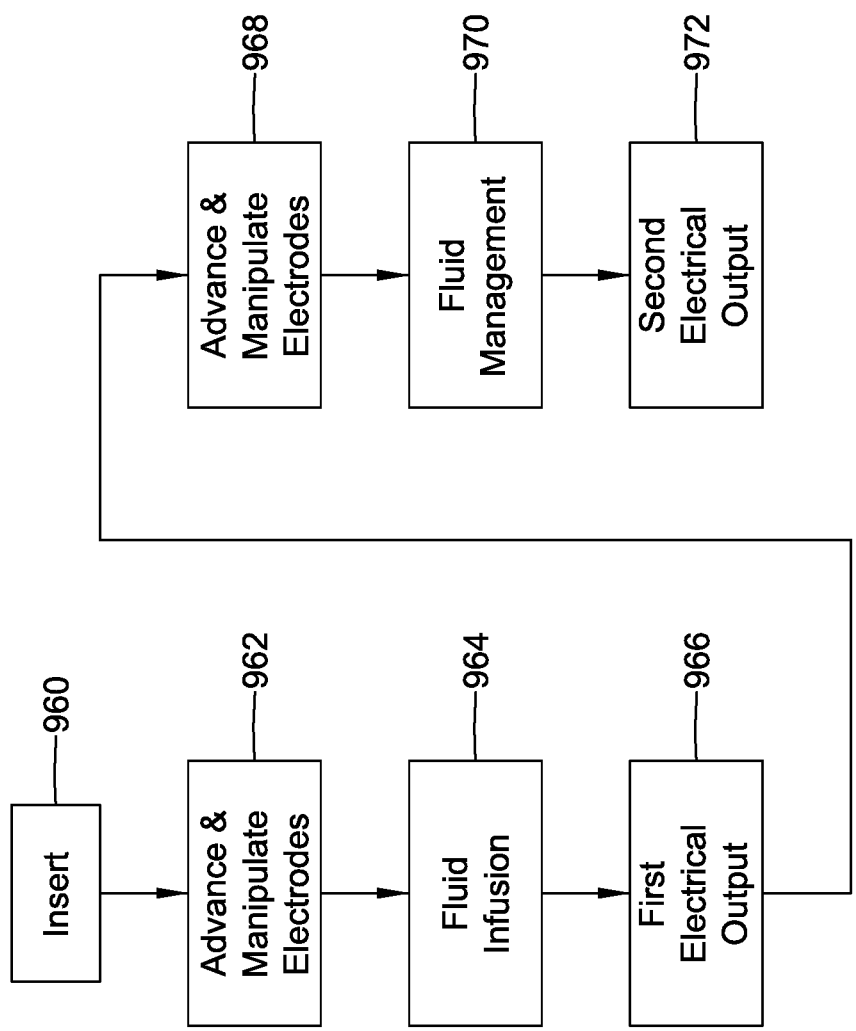

FIG. 19 shows a still further example. Here, a therapy apparatus is inserted at 960, and electrodes thereof may be advanced and/or manipulated into a desired use configuration as noted at 962. Fluid infusion may follow at 964, followed by a first therapy which may be electrical as indicated at 966. The electrodes may again be advanced and/or manipulated, as indicated at 968. Steps 962 and 968 may include, for example, advancing, retracting, selecting, deselecting, and/or changing the exposed surface are of one or more electrodes. Fluid management is performed at 970 by, for example, infusing or extracting fluid, if desired. For example, if saline is injected at 964 to reduce impedance and generate increased current flow at a given voltage, extraction of the saline (and at least some associated biological media with which the saline will have mixed) may raise impedance for purposes of delivering a second electrical output 972, thereby reducing heating associated with the second output 972. Fluid may be extracted at 970 for purposes of determining whether therapy has been effective at block 968, as the extracellular fluid constituents may indicate whether cells have been destroyed or otherwise affected, for example.

Figure 20:
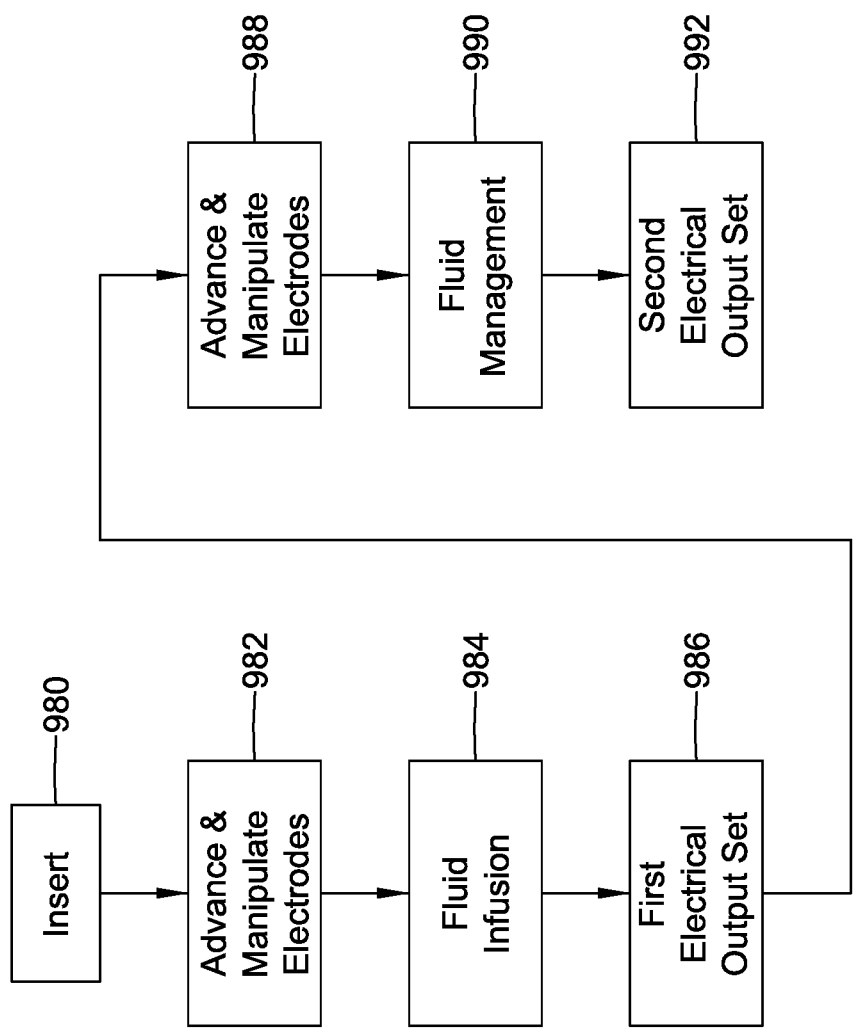

FIG. 20 shows another example. Here, a therapy apparatus is inserted at 980 and electrodes thereof may be advanced and/or manipulated into a desired use configuration as noted at 982. Fluid is then infused as noted at 984, and a first set of electrical outputs is delivered. For example, outputs to generate thermal effects may be delivered as part of a first set, followed by outputs to generate IRE effects, using different selection of electrodes as desired within the therapy set 986. The electrodes are then advanced and/or manipulated as indicated at 988, fluid management 990 is performed (such as injecting or withdrawing fluid), and a second electrical output set is delivered at 992. In an example, the first and second electrical output sets comprise each of thermal and IRE outputs, such that the possibility of tract seeding is eliminated in block 986 prior to moving or manipulating electrodes in block 988, as well as before ending the therapy method at block 992.

The examples of FIGS. 16-20 are illustrative of a number of combinations that may be possible with a versatile apparatus as disclosed herein having the ability to manipulate shaft electrode size and location during the procedure and, if desired, between therapy delivery steps. The skilled artisan will appreciate additional variations and adaptations that may be readily achieved with this novel apparatus.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of ablating a tissue region using a cannula having a shaft with proximal and distal ends, and one or more tissue penetrating electrodes passing through the shaft and moveable relative to the shaft, the method comprising:
  inserting the cannula to place the distal end of the shaft at a desired location near a target tissue;
  applying a grounding pad to the patient;
  advancing at least one of the one or more tissue penetrating electrodes beyond the distal end of the shaft to pierce tissue;

delivering a first waveform adapted to cause thermal ablation in a first region relatively nearer to the at least one tissue penetrating electrode;

delivering a second waveform adapted to cause irreversible electroporation in a second region relatively more distant from the at least one tissue penetrating electrode;

wherein the shaft has a shaft electrode thereon and the cannula comprises a sheath adapted to be moveable relative to the shaft to cover or uncover all or portions of the shaft electrode; and wherein the first waveform is delivered using the grounding pad and at least one of the one or more tissue penetrating electrodes as an electrode for therapy delivery, and the second waveform is delivered using the shaft electrode and at least one of the one or more tissue penetrating electrodes.

2. The method of claim 1 wherein the sheath adapted to be moveable relative to the shaft to cover or uncover all or portions of the shaft electrode, the method further comprising manipulating the sheath to expose a first area of the shaft electrode while the first waveform is delivered, and manipulating the sheath to expose a second area of the shaft electrode while the second waveform is delivered, wherein the first and second areas are different from one another, further wherein each of the first and second waveforms are delivered using at least one of the one or more tissue penetrating electrodes and the shaft electrode as opposing poles for an electrical output.

3. The method of claim 1 wherein the shaft comprises a fluid infusion lumen having an opening near the distal end thereof, the method further comprising infusing a fluid through the fluid infusion lumen prior to delivering the first waveform, the fluid adapted to dampen a thermal effect of the first waveform for a first volume of tissue.

4. The method of claim 1 wherein the shaft comprises a fluid infusion lumen having an opening near the distal end thereof, the method further comprising infusing a fluid through the fluid infusion lumen prior to delivering the first waveform, the fluid adapted to enhance a thermal effect of the first waveform for a first volume of tissue.

5. The method of claim 1 wherein the shaft comprises a fluid infusion lumen having an opening near the distal end thereof, the method further comprising infusing a fluid through the fluid infusion lumen prior to delivering the second waveform, the fluid adapted to enhance the electrical effect of the second waveform.

6. The method of claim 1 wherein the first and second waveforms are each delivered repeatedly by alternating between the first and second waveforms.

7. The method of claim 1 wherein the first waveform is delivered using a first of the at least one tissue penetrating electrodes, and the second waveform is delivered using a second of the at least one tissue penetrating electrodes.

8. The method of claim 1 wherein the first waveform is delivered repeatedly in a first therapy set, and the second waveform is delivered repeatedly in a second therapy set.

9. The method of claim 8 further comprising repositioning the one or more tissue penetrating electrodes after the first therapy set and before the second therapy set.

10. The method of claim 1 wherein at least the second waveform induces each of reversible electroporation in a third region, and irreversible electroporation in the second region, the method further comprising infusing a fluid adapted to cause cell death to the third region.

* * * * *